United States Patent [19]

Wang

[11] Patent Number: 5,454,260
[45] Date of Patent: Oct. 3, 1995

[54] NON DESTRUCTIVE ADHESION TESTING

[75] Inventor: Yucong Wang, Saginaw, Mich.

[73] Assignee: General Motors Corporation, Detroit, Mich.

[21] Appl. No.: 170,144

[22] Filed: Dec. 20, 1993

[51] Int. Cl.⁶ .................................................. G01N 19/04
[52] U.S. Cl. ............................ 73/150 A; 73/37; 73/821; 73/825
[58] Field of Search .................. 73/150 A, 821, 73/825, 827, 830, 37

[56] References Cited

U.S. PATENT DOCUMENTS

| | | | |
|---|---|---|---|
| 3,581,557 | 6/1971 | Drees et al. | 73/37 |
| 3,770,593 | 10/1973 | Dick | 204/1 T |
| 4,393,699 | 7/1983 | Seiler, Jr. | 73/150 A |
| 4,413,510 | 11/1983 | McCusker et al. | 73/150 A |
| 4,606,225 | 8/1986 | Thomason et al. | 73/150 A |
| 4,715,007 | 12/1987 | Fujita et al. | 364/563 |
| 4,819,489 | 4/1989 | Nelson et al. | 73/854 |
| 4,895,029 | 1/1990 | Yamada et al. | 73/827 |
| 5,027,650 | 7/1991 | Oblas et al. | 73/150 A |
| 5,056,356 | 10/1991 | Kuhns et al. | 73/49.2 |
| 5,079,958 | 1/1992 | Takase et al. | 73/862.64 |
| 5,085,084 | 2/1992 | Salatino | 73/827 |
| 5,214,963 | 6/1993 | Widder | 73/827 |
| 5,315,861 | 5/1994 | Egan et al. | 73/150 A |
| 5,341,685 | 8/1994 | Malone | 73/827 |

Primary Examiner—Diego F. F. Gutierrez
Attorney, Agent, or Firm—Lawrence B. Plant

[57] ABSTRACT

Non destructive adhesion testing of coatings to substrates. A supersonic jet of water is impinged against the coating. The impingement intensity of the jet is set at a predetermined "failure intensity" determined by testing of a sample having a minimum acceptable level of adhesion. Parts passing through the supersonic jet unscratched pass the test. Parts whose coatings debond when impacted by the jet fail the test.

12 Claims, 1 Drawing Sheet

NON DESTRUCTIVE ADHESION TESTING

This invention relates to a process for the non-destructive testing of a plurality of coated articles on a production line to determine the sufficiency of the coating's adhesion to the substrate.

BACKGROUND OF THE INVENTION

It is known to coat a variety of substrates (e.g., metal, plastic, ceramic, etc.) with a variety of coatings (e.g., metal, paint, etc.) for engineering and aesthetic purposes. These coatings may be deposited by brush, spray, electrolysis, electrophoresis, dipping, etc. Over the years, a variety of well-known adhesion tests have been devised for evaluating the strength of the bond between the coating and the substrate. Common such tests include: (1) the "tape" test wherein adhesive tape is applied to the coating and then pulled off normal to the surface to see if the coating pulls off with the tape or adheres to the substrate; (2) the "bend" test wherein a test sample is bent to a predetermined angle (e.g., 90 degrees) to see if the coating cracks and bonds at the bend site; (3) the "stud pull" test wherein the coating is applied to a stud with an adhesive and the tensile stress required to separate the coating from the substrate measured; (4) the "shear" test wherein the coated surfaces are adhered together and shear stress applied thereto until failure occurs; (5) the "microscratch" test wherein the coating is scratched with a particular tool under a particular load, and the scratch produced characterized by a tool friction measurement, and acoustic emission detection and microscopy; and (6) the "glass bead" test wherein a stream of air-borne glass beads (e.g., $SiO_2$, $Al_2O_3$, or mixtures thereof) are impinged upon the coated part at a specified intensity which causes delamination and/or blistering of coatings which have unacceptable adhesion to their substrate. The "glass bead" test is used most frequently in connection with production lines to test a significant percentage of the parts coming down the line to screen out parts having unacceptable adhesion. The production line test involves: (1) cleaning of the parts to be tested so that the glass beads do not become contaminated; (2) positioning the parts a predetermined stand-off distance (e.g., 4 inches) from the nozzle from which the glass beads emanate; (3) setting the gas pressure (e.g., 70 psi) for the air used to propel the glass beads; (4) impinging the beads against the parts to be tested for a predetermined time (e.g., 4 seconds); (5) cleaning the glass beads from the tested parts; and (6) recycling the glass beads for reuse. Among the disadvantages of this process are the general undesirability of dealing with air-borne ceramic beads in a plant environment, time consuming and costly pre-cleaning and post-cleaning of the parts before and after testing, and wear on the equipment used to handle and propel the glass beads.

It is known in the art to provide internal combustion engine aluminum pistons with scuff and wear resistant metal coatings. Such coatings as iron, nickel-tungsten (3% w), nickel-cobalt (3% Co) or composite coatings comprising ceramic particles/fibrils (e.g., SiC) electrolytically codeposited with a metal, e.g., nickel, are known. Sprayed or vapor deposited coatings are also known. It is desirable to test a significant number (e.g., 10% or more) of coated pistons to insure that the deposition parameters consistently yield adequate coating adhesion so that no unsatisfactory pistons are assembled into an engine since the cost of engine repair and/or piston replacement after the engine is assembled and installed in a vehicle is so costly.

It is an object of the present invention to provide a simple, reliable, cost effective process for determining the sufficiency of adhesion between a coating and its substrate which process can be used as a quality control tool to "go/no-go" test and evaluate a significant percentage of parts travelling down a production line, and all without need for pre-cleaning and post-cleaning of the parts before and after testing and/or cleaning and recycling of ceramic media used in the test. This and other objects and advantages of the present invention will become more readily apparent from the detailed description thereof which follows.

BRIEF DESCRIPTION OF THE INVENTION

The present invention comprehends a method for testing a plurality of coated parts (e.g., I/C engine pistons) on a production line to determine whether the coating is sufficiently adherent to the substrate to satisfy the intended use requirements of the part being tested. A part like that to be tested is prepared under controlled conditions to provide a sufficient level of adhesion of a desired coating. This part is then used as a standard against which all other parts are compared and is used to set the intensity of a supersonic water jet adhesion testing device. More specifically, the "standard" part is fixtured and positioned in precisely the same manner as the parts to be tested will be fixtured and positioned on the production line adjacent an identical nozzle to that to be used on the production line. Thereafter, a supersonic (i.e., greater than ca. 1088 ft/sec) reference jet of water is propelled from the nozzle against at least one, and preferably many, site(s) on the standard part and the intensity of the reference jet's impingement on the part increased until blistering or bonding of the coating occurs (i.e., the "failure intensity"). This failure intensity is measured and determines the intensity that is required to debond the coating from an acceptable part, i.e., one whose adhesion is adequate to meet the performance requirement of the part. The conditions used in connection with the reference jet of water when determining the failure intensity are then duplicated adjacent a production line where the production parts are to be similarly tested. A "screening" jet adjacent the production line is then set to the failure intensity determined as set forth above and all the parts coming down the line are subjected to the screening water jet to determine if they have acceptable levels of adhesion. More specifically, a nozzle like that used to test the standard part is positioned adjacent the production line for propelling a supersonic screening jet of water against at least one, and preferably many, target site(s) on the coated substrates whose coatings' adhesion are to be evaluated. The impingement intensity of the screening jet is set at or below the failure intensity determined in the test made on the standard part. Thereafter, all of the parts to be tested are paraded through the screening jet so as to impinge the screening jet against the target site(s). Those parts whose coatings debond from impingement of the screening jet thereon are separated from those that do not.

According to a preferred embodiment of the invention the screening jet itself will comprise a confluence of a plurality of smaller streams emanating from a plurality of orifices in the end of a rotating nozzle so to provide a screening jet which impinges on the target site(s) with substantially uniform pressure. In accordance with a most preferred embodiment of the invention, the nozzle and the part to be tested move relative to each other such that the screening jet contacts a plurality of target sites on the part being tested.

The impingement intensity may be determined in a variety of ways, but is most simply determined by measuring the pressure of the water in the conduit behind the nozzle. This pressure is varied as needed, i.e., to vary the intensity of the water jet on the target site, by simply varying the output of the intensifier pump supplying the water to the nozzle.

In accordance with one specific application of the invention, aluminum pistons are coated with metals (e.g., nickel or iron) with or without ceramic particles entrained therein, and then subjected to a supersonic jet stream of water having impingement intensities between about 10,000 psi and 55,000 psi of pressure behind the nozzle (i.e., depending on the nature of the coating) when it is spaced 1.6 inches from the target site(s) and jets about 1.2 to about 2.0 gals/min of water flows at supersonic velocities through four orifices each having a diameter of 0.009 inch.

BRIEF DESCRIPTION OF THE DRAWINGS

The invention will better be understood when considered in the light of the following detailed description of a specific embodiment thereof which is provided hereafter in conjunction with the several drawings in which.

DETAILED DESCRIPTION OF SPECIFIC EMBODIMENTS OF THE INVENTION

While hereafter the invention will be described and illustrated in connection with the testing of metal coatings on aluminum pistons it is to be understood that it is equally applicable to other substrates and other coatings as well, and that the steps and principals embodied in the process are applicable to a wide variety of materials and shapes.

Figure 2:
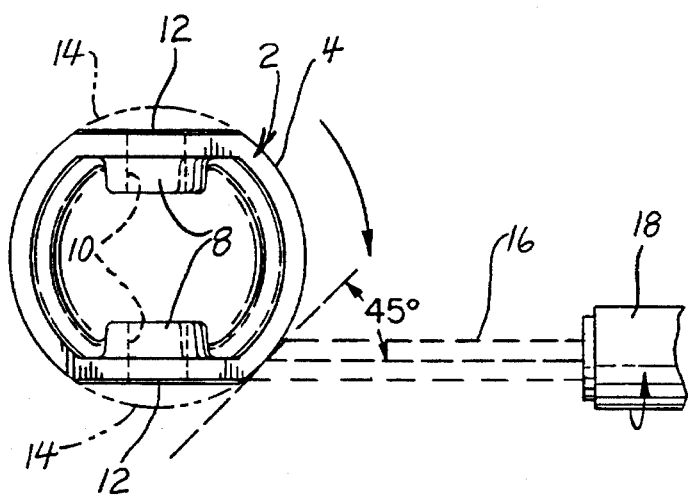
FIG. 2 is a plan view of the device of FIG. 1.

The Figures show a piston 2 with an exterior surface 4 having an electrodeposited coating 6 thereon. The piston 2 includes two journals 8 having openings 10 therethrough extending to the flat surfaces 12 on opposite walls thereof and adapted to receive a wrist pin (not shown). The flat surfaces 12 need not be plated and accordingly are protected from the supersonic jet 16 of water emanating from the nozzle 18 by shields 14. The piston 2 is nested in a fixture 20 which, in turn, is mounted on a spindle 22 for effecting rotation of the piston 2 in the direction shown by the arrow 24. The nozzle 18 is caused to rotate at a high speed (i.e., ca. 1000 rpm) by means of a motor 26 both of which are carried by a hollow shaft 28 which moves up and down relative to the piston 2 as indicated by the arrow 30. Pressurized water from a pump (not shown) is fed to the nozzle 18 through the hollow center 32 of the shaft 28. As best shown in FIG. 2, the supersonic water jet 16 will impinge on the external surface 4 of the piston 2 at an acute angle, and preferably at about 45 degrees, to the tangent of the piston surface.

In accordance with the invention, a supersonic jet(s) of water is provided by means of a high pressure intensifier pump which is capable of providing up to as much as 55,000 lbs/inch$^2$ of pressure in the conduit behind one or more small orifices 34 in a nozzle 18. The nozzle 18 is caused to rotate at a high speed (i.e., about 1000 rpm) such that the individual jet streams are essentially merged at the impact site and to provide a substantially uniform pressure on the impact site. The velocity of the jet stream, and hence its intensity, will be at least about 1082 ft/sec. The velocity may be increased substantially by increasing the output of the intensifier pump so as to increase the pressure of the water behind the orifices 34. A number of factors will affect the intensity with which the jet stream impinges on the part being tested. The rate at which the nozzle rotates and traverses the part, the distance between the nozzle and the part, the velocity of the water flow, the size of the target site and the impingement angle all influence the test.

For purposes of determining the intensity to be used on the production line, a test is first conducted on a standard. The standard is identical to the parts being tested but is prepared under controlled conditions so as to provide a coating that has the minimum acceptable adhesion between the coating and the substrate. The standard part is then fixtured in exactly the same way the parts to be tested and positioned in exactly the same relationship to the jet tester's nozzle (i.e., impact angle, stand-off distance, travel speed, etc.). Water pressure behind the nozzle 18, and hence the velocity of the water jet, is then progressively increased until the coating blisters or otherwise debonds from the target. The pressure where debonding occurs is a measure of the failure intensity of the stream, and this pressure is then used to set the pressure of the screening jet to be used on the production line. Thereafter the production parts to be tested are paraded through the screening jet. Those parts whose coatings debond from the substrate fail the test and are separated from those which successfully pass the test.

Measuring the pressure of the water behind the nozzle is the most convenient way to measure the intensity of the jet all other variables remaining equal. For each coating (i.e., composition, thickness, etc.) and substrate combination, the failure intensity will be different and the pressure behind the nozzle at which the coating starts to debond will be different. Regardless whatever the variables might be in determining the failure intensity, once the failure intensity has been established it is then used as a basis to screen the adhesion of the coatings on other arts evaluated under the same conditions.

Figure 1:
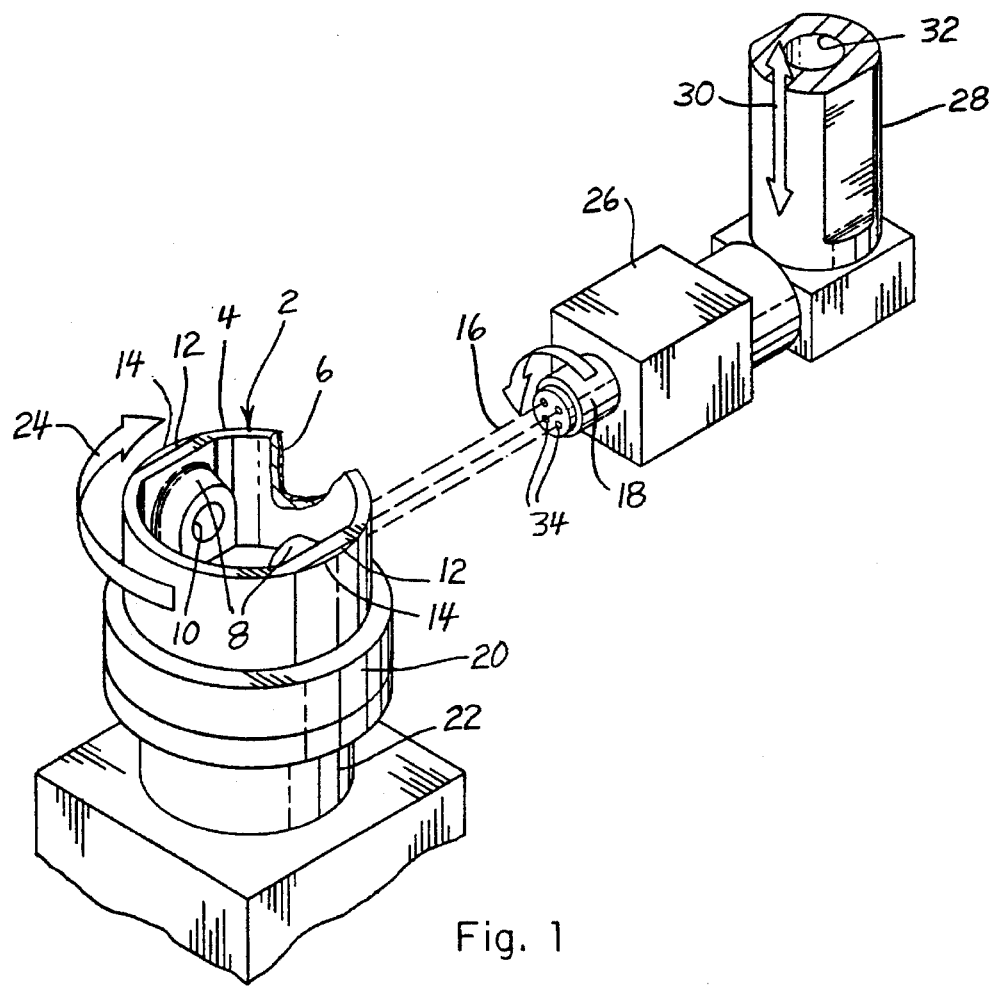
FIG. 1 is an isometric view of a supersonic jet adhesion testing device for coatings on an internal combustion engine piston.

In one specific example of the invention, the water jet apparatus was made by the Ingersol Rand Corp. and included four orifices 34 in the rotating nozzle 18 shown in FIG. 1. The orifices each had a diameter of about 0.009 inches, were spaced about 0.5 inches from each other and emitted water speeds up to 3,000 ft/sec. The nozzle rotated at 1,000 rpm and moved up and down relative to the piston 2 at a speed of about 2 in/min. The jet 16 emanating from the nozzle 18 contacted the arcuate surface 4 of an aluminum piston 2 at an angle of 45 degrees from the tangent, while the piston 2 itself rotated at a rate of about 100 rpm. The distance between the nozzle 18 and the target site on the piston was 1.6 inches. Depending on the pressure behind the nozzle, the size of the impingement site would vary but was essentially circular in nature. The amount of water used was in the range of 1.2 to 2.0 gals/min again depending on the water pressure which varied from 10,000 psi to 55,000 psi. When the water pressure exceeded 20,000 psi, uncoated areas (e.g., the flats 12) were masked or otherwise shielded from the jet to avoid water blasting damage to those areas. The fixture 20 masked other portions of the piston 2 which were not to be tested. Angling the jet at 45 degree to the tangent provided the maximum shear stress to the coating, and hence stressed the coating the most with the least pressure behind the nozzle 18.

While the invention has been disclosed primarily in terms of certain embodiments thereof it is not intended to be limited thereto but rather only to the extent set forth hereafter in the claims which follows.

The embodiments of the invention in which an exclusive property or privilege is claimed as defined as follows:

1. A process for determining acceptable adhesion of a coating to a substrate comprising the steps of:

a. preparing a reference standard by depositing a reference coating onto a reference substrate such that said reference coating adheres to said reference substrate with a minimum acceptable strength;

b. directing a supersonic reference jet of water from a reference nozzle against at least one site on said reference coating;

c. varying the impingement intensity of the reference jet until a failure intensity is ascertained where said reference coating debonds from said reference substrate;

d. measuring said failure intensity;

e. parading a plurality of coated substrates having the coating to be evaluated through a supersonic screening jet of water emanating from an evaluation nozzle so as to impinge said screening jet onto at least one target site on said coating to be evaluated, said screening jet being adjusted to impinge on said at least one target site with an impingement intensity of at least about said failure intensity; and f. separating those coated substrates whose coatings debond from the substrate from those that adhere to the substrate when subjected to said screening jet.

2. A process according to claim 1 wherein said screening jet is directed against a plurality of sites on said substrates to be evaluated.

3. A process according to claim 2 wherein said nozzles and said substrates move relative to each other.

4. A process according to claim 3 wherein said substrates are pistons for an internal combustion engine and said coatings are on annular surfaces of said pistons.

5. A process according to claim 4 wherein said jets are directed against said sites at an acute angle to the tangent to said annular surfaces.

6. A process according to claim 5 wherein said acute angle is about 45°.

7. A process according to claim 4 wherein said pistons comprise aluminum and said coatings comprise a metal.

8. A process according to claim 7 wherein said coatings include discrete ceramic particles dispersed throughout said metal.

9. A process according to claim 1 wherein said evaluation nozzle for generating said screening jet includes a plurality of orifices and rotates rapidly such that said screening jet impinges on said at least one target site with substantially uniform pressure.

10. A process according to claim 9 wherein said substrates comprise aluminum, said coatings comprise a metal selected from the group consisting of iron and nickel, and said impingement intensity is between about 10,000 psi and 55,000 psi when said evaluation nozzle is spaced about 1.6 inches from said at least one target site and contains exit orifices having a diameter of 0.009 inch through which about 1.2 to about 2.0 gals/min of water flows.

11. A process according to claim 1 wherein said failure intensity is determined by measuring the water pressure behind the nozzle.

12. A process according to claim 1 wherein said jets are directed against said coatings at an acute angle to said sites.

* * * * *